US012109398B2

(12) United States Patent
Gjoedesen et al.

(10) Patent No.: US 12,109,398 B2
(45) Date of Patent: Oct. 8, 2024

(54) TORSION SPRING DRIVEN INJECTION DEVICE

(71) Applicant: Novo Nordisk A/S, Bagsvaerd (DK)

(72) Inventors: Claus Urup Gjoedesen, Holte (DK); Niels Christian Egholm Soerensen, Hilleroed (DK); Kim Roennow Sejtzer, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 751 days.

(21) Appl. No.: 17/286,845

(22) PCT Filed: Oct. 28, 2019

(86) PCT No.: PCT/EP2019/079394
§ 371 (c)(1),
(2) Date: Apr. 20, 2021

(87) PCT Pub. No.: WO2020/089167
PCT Pub. Date: May 7, 2020

(65) Prior Publication Data
US 2021/0386933 A1    Dec. 16, 2021

(30) Foreign Application Priority Data

Oct. 30, 2018  (EP) .................................... 18203370

(51) Int. Cl.
*A61M 5/20*   (2006.01)
*A61M 5/315*  (2006.01)
*A61M 5/31*   (2006.01)

(52) U.S. Cl.
CPC ...... *A61M 5/2033* (2013.01); *A61M 5/31526* (2013.01); *A61M 5/31543* (2013.01); *A61M 5/3157* (2013.01); *A61M 5/31585* (2013.01); *A61M 5/31591* (2013.01); *A61M 2005/2073* (2013.01); *A61M 2005/3126* (2013.01)

(58) Field of Classification Search
CPC ................ A61M 5/24; A61M 5/31553; A61M 5/31583; A61M 5/31541; A61M 5/31593
See application file for complete search history.

(56) References Cited

U.S. PATENT DOCUMENTS 9,687,611 B2    6/2017 Moeller et al.
10,004,852 B2 *  6/2018 Marsh ................. A61M 5/3155
(Continued)

FOREIGN PATENT DOCUMENTS

CN    108601909 A    9/2018
EP       338806      10/1989
(Continued)

*Primary Examiner* — Laura A Bouchelle
(74) *Attorney, Agent, or Firm* — Wesley Nicolas

(57) ABSTRACT

The invention relates to a torsion spring driven injection device for ejecting set doses of a liquid drug. In a first aspect the torsion spring driven injection device is provided with a blocking structure which is operated by the rotatable display element such that the set dose can only be expelled when a certain minimum dose size has been set. In a second aspect the torsion spring driven injection device is provided with a release mechanism which secures that the set dose can only be expelled as one single full dose in one stroke. The two aspects can easily be combined such that the predetermined minimum dose size most be expelled as one single dose.

17 Claims, 5 Drawing Sheets

(56) References Cited

U.S. PATENT DOCUMENTS

| | | | |
|---|---|---|---|
| 10,806,865 | B2 | 10/2020 | Cowe |
| 2019/0038842 | A1 | 2/2019 | Pedersen et al. |

FOREIGN PATENT DOCUMENTS

| | | | |
|---|---|---|---|
| JP | 2016163721 | A | 9/2016 |
| WO | 2012049140 | A1 | 4/2012 |
| WO | 2014161952 | A1 | 10/2014 |
| WO | 2014161954 | A1 | 10/2014 |
| WO | 2016083384 | A1 | 6/2016 |
| WO | 2017102395 | A1 | 6/2017 |

* cited by examiner

TORSION SPRING DRIVEN INJECTION DEVICE

CROSS-REFERENCE TO RELATED APPLICATIONS

This application is a 35 U.S.C. § 371 National Stage application of International Application PCT/EP2019/079394 (published as WO 2020/089167), filed Oct. 28, 2019, which claims priority to European Patent Application 18203370.4, filed Oct. 30, 2018; the contents of which are incorporated herein by reference.

THE TECHNICAL FIELD OF THE INVENTION

The invention relates to an automatic torsion spring driven injection device having a mechanical and rotatable display for showing the size of the dose being set. More specifically, the invention relates to such torsion spring driven device wherein the user can only perform an injection once a minimum dose size has been set.

The invention also relates to such torsion spring injection device wherein the set dose is ejected as a full dose and wherein the dose button can only be re-activated once the full dose has been ejected.

DESCRIPTION OF RELATED ART

Automatic injection devices wherein a torsion spring drives the ejection of the liquid medicament has been known for decades. EP 338,806 discloses an example of such torsion spring driven injection device in which the user strains the torsion spring by rotating a rotatable dose setting element provided at a proximal end of the pen-shaped injection device. The indicia showing the size of the dose being set is printed on the outer surface of the rotatable dose setting button and the dose setting button is consequently limited to rotating less than one full rotation. This clearly limits the maximum size which a use can set as only the periphery of the dose setting button is available for carrying indicia.

Another example of such torsion spring driven injection device is provided in U.S. Pat. No. 9,687,611. This injection device has the indicia printed in a helical row on a rotatable scale drum which is helically threaded to the housing. This allows the scale drum to rotate several rotations which highly increases the number of indicia which can be printed onto the scale drum.

An injection device of this type has successfully been commercialized by the company Novo Nordisk NS under the trade name FlexTouch® which injection device is e.g. disclosed in FIG. 1-3 in the present application.

All though a high number of different dose size settings are possible using such injection devices there are sometimes the need for only expelling one predetermined dose size and to ensure that the torque in the torsion spring can only be released to expel the set dose once the user has, as a minimum, set the full predetermined dose size.

Further, for some drugs it is beneficial if the full dose is delivered in one stroke without pausing the dose expelling.

DESCRIPTION OF THE INVENTION

It is an object of the present invention to provide a torsion spring driven injection device wherein the set dose can only be expelled once the intended full dose size has been set by the user.

It is a further object to provide a similar torsion spring driven injection device wherein the full dose must be expelled as one single full dose.

Accordingly, in a first aspect of the present invention a torsion spring driven injection device is provided. The injection device comprises:
- a housing structure which holds a container containing the liquid drug to be ejected. The container is preferably a traditional cartridge secured in the housing structure and preferably permanently secured in a non-removal manner,
- a rotational dose setting element which is operable by a user for setting the size of a set dose to be ejected,
- a rotatable dose setting structure which structure transfer rotation from the dose setting element to a straining of a torsion spring such that a torque is stored in the torsion spring upon rotation of the dose setting element,
- a rotatable display element which is coupled to the dose setting structure to follow rotation of the dose setting structure for displaying the size of the set dose to be ejected. The display element is helically movable relatively to, and preferably inside, the housing structure from an initial position to a dosing position,
- a piston rod arranged in a longitudinal direction and movable in a distal direction to drive out the set dose from the container,
- a rotatable drive element which engages the piston rod and are adapted to move the piston rod in the distal direction upon rotation of the rotatable drive element, and
- an axially movable release element for releasing the torque stored in the torsion spring to rotate the rotatable drive element.

The torsion spring driven injection device further comprises a blocking structure which is operable between a first position and a second position, and wherein
- the blocking structure in the first position prevents axial movement of the release element, and
- in the second position allows axial movement of the release element.

Accordingly, the blocking structure is operational by the rotatable display element.

It is thus possible to set the release element free to move axially by use of the rotatable display element. Preferably, the blocking structure default prevents axial movement of the release element but whenever the rotatable display element is rotated or otherwise moved to a specific axial and/or rotational position it activates the blocking structure such that the release element becomes axially movable to thereby release the set dose.

The specific axial and/or rotational position of the rotatable display element is thus the minimum dose size the user needs to set before being allowed to eject the set dose and is predetermined by the manufacturer of the injection device.

An injection device according to the above further has the possibility to operate as a so-called multi-use fixed dose injection device wherein a predefined plurality of predefined dose volumes are decided by the manufacturer of the injection device. The minimum dose sizes predetermined by the manufacturer can be determined to also be the maximum allowable dose size which means that all the doses to be expelled are the same in size, at least in volume. In one example, the container could e.g. contain 3.0 ml of a liquid drug and the dose volumes to be expelled could e.g. be predetermined to be 0.6 ml in volume understood such that both the minimum and the maximum dose is predetermined to be 0.6 ml. The user would in such scenario only have the possibility of setting and expelling identical dose volumes and in this example it would henceforth be possible to expel 5 identical dose volumes of 0.6 ml.

The rotatably display element is preferably coupled to the dose setting structure such that the rotatably display element follows rotation of the dose setting structure. The rotatable display element, e.g. the scale drum, is thus coupled to follow all rotation of the dose setting structure. In one example the dose setting structure comprises a ratchet tube which is associated with the rotatable display element by a groove and tongue engagement. The display element thus follows rotation of the ratchet tube both when setting a dose, when correcting a dose and when expelling a dose.

The rotatably display element preferably carries indicia engraved or printed on the display element to indicate to the user that the intended dose is reached. These indicia are not necessarily Arabic numbers but can be any kind of indicia which visually communicates a message to the user.

The rotatable display element preferably moves helically by being coupled to the housing structure and thus guided by a helical interface which in one example could be a threaded connection. Thus, during does setting, the display element is moved helically to a position wherein it releases the blocking structure.

Further, the release element is coupled to the dose setting structure preferably by being coupled to the ratchet tube such that the release element follows axial movement of the ratchet tube. The coupling between the ratchet tube and the release element is preferably such that the release element is able to rotate relatively to the ratchet tube but is axially locked to the ratchet tube.

The ratchet tube is preferably coupled to follow axial movement of a reset tube. In one example the ratchet tube and the reset tube are moulded as one component and in another preferred example the ratchet tube and the reset tube are coupled to move together in the axial direction but allowed to rotate relatively to each other at least a few degrees.

The release element is movable axially in the distal direction during dosing such that the release element engages with the rotatable drive element. The release element is preferably moved axially by the dose setting structure.

Henceforth, when the user moves the dose setting structure axially in the distal direction, the release element follows this movement and thus engages the rotatable drive element. At the same time as the release element engages the rotatable drive element it releases from the housing such that the torsion spring can rotate the release element by rotating the ratchet tube. The simultaneous rotation of the ratchet tube and the release element is thus transferred to a similar rotation of the drive element which rotation thus drives the piston rod forward.

Further, the dose setting structure is provided with one or more flexible locking arms which engages the housing structure in the default state such that the dose setting structure is prevented from moving in the axial direction. It is henceforth not possible for the user to move the dose setting structure in the distal direction and release a dose as long as the locking arm of the dose setting structure engages the housing structure.

The kinematic reversal wherein the flexible arms are provided on the housing structure is also possible.

In a specific example, the locking arm is provided on the ratchet tube which together with the reset tube makes up the dose setting structure. The dose setting structure is thus rotatable by rotation of the dose setting element and the rotation of the dose setting element and the dose setting structure results in a straining of the torsion spring. All though, the locking arm is both here and in other passages referred in singularity any number of locking arms can be provided.

In order to prevent axial movement of the dose setting structure, the housing structure thus engages with the flexible locking arm to thereby prevent axial movement of the ratchet tube. Axial movement of the dose setting structure thus requires that the housing structure and the locking arm disengages. Such disengagement is preferably done by the rotatable display element. During the helical movement of the rotatable display element it engages with the locking arm at a specific position whereby the rotatable display element activates or bends the locking arm (or arms) away from the housing structure.

The locking arm thus moves away from the housing structure when a predetermined dose size has been reached. The predetermined dose size is the dose size which is set when the rotatable display element reaches the specific release position. Henceforth the predetermined dose size is a minimum dose as it could be possible to further rotate the rotatable display element after the flexible arm has been moved away from the housing structure. However, means can be provided for preventing the further rotation of the rotatable display member such that the minimum dose and the maximum are the same as explained.

In a further example the housing structure is on the inner surface provided with a flange structure engaging the locking arm(s) to prevent axial movement of the ratchet tube and the rotatable display element bends the locking arm(s) away from the flange structure at a specific position of the rotatable display element relatively to the housing structure.

It is a further object of the present invention to provide a torsion spring driven injection device wherein the full dose must be expelled as one single full dose in one stroke.

Accordingly, in a first aspect of the present invention a torsion spring driven injection device is provided. The injection device comprises:

a housing structure which holds a container containing the liquid drug to be ejected. The container is preferably a traditional cartridge secured in the housing structure,
  a rotational dose setting element which is operable by a user for setting the size of a set dose to be ejected,
  a rotatable dose setting structure which transfer rotation from the dose setting element to a straining of a torsion spring such that a torque is stored in the torsion spring upon rotation of the dose setting element,
  a rotatable display element which is arranged to follow rotation of the dose setting structure for displaying the size of the set dose to be ejected. The display element is helically movable relatively to, and preferably inside, the housing structure from an initial position to a dosing position,
  a piston rod arranged in a longitudinal direction and movable in a distal direction to drive out the set dose from the container,
  a rotatable drive element which engages the piston rod and are adapted to move the piston rod in the distal direction upon rotation of the rotatable drive element, and
  an axially movable release element for releasing the torque stored in the torsion spring to rotate the rotatable drive element.

Further, the release element is, preferably on an outer surface, provided with one or more teeth engaging corresponding teeth provided on the rotatable drive element and a torque preferably arising from the torsion spring is transferred from one or more teeth of the release element to the corresponding teeth on the rotatable drive member such that a rotation of the release element during dosing is transferred to a rotation of the rotatable drive element. The teeth provided on the release element are thus slidable in the axial direction in relation to the corresponding teeth on the rotatable drive element.

According to the second aspect of the present invention, at least one of the corresponding teeth on the rotatable drive element is proximally provided with a radial extension which hinders the teeth and thus the release element from sliding in the axial direction in relation to the corresponding teeth and the rotatable drive element when a torque above a certain threshold value is being applied to the teeth by the torsion spring.

During dose expelling the torsion spring rotates the ratchet tube and thus also the release member. The rotation of the release member applies a torque onto the drive element which creates an axial friction between the surfaces of the teeth on the release member and the teeth on the drive element. However, the friction is such that the teeth are able to slide axially.

In the second aspect however, a radial extension is provided on at least one of the teeth on the rotatable drive member. This radial extension prevents the teeth on the release element from moving in the proximal direction as long as a torque is being transferred. The result is thus that as long as the torsion spring applies a sufficient torque to the release element and further onto the rotatable drive member, the release element is prevented from moving in the proximal direction. However, when the torque falls below a certain threshold value, the teeth on the release element is able to slide axially pass the radial extension on the corresponding teeth on the rotatable drive member and into re-engagement with the housing structure.

Consequently, the reset tube and the injection button remain depressed as long as the torsion spring drives the release element and the drive element. Once the release element stops to rotate, no torque is applied onto the drive element and the release element is thus able to move in the proximal direction.

The release element stops to rotate either when the torque stored in the torsion spring has been used or when the release element carried by the ratchet tube is physically stopped as this would hinder the remaining torque in being transferred to the rotatable drive element. In one example such physical stop could be when the scale drum reaches its zero position.

The shape and the size of the radial extension can be designed such that the release element can only move back to the initial position when a predetermined balance between the torque applied and the force of the return spring is obtained.

In a further embodiment, the shape of the radial extension can be formed such that it permanently locks the teeth on the release element and thus the release element from axial movement at least in the proximal direction. In such case the user can only activate the injection button once where after the injection button will remain depressed forever. The injection device would thus be categorized as a one-shot device.

The two different aspect of the present invention can also be combined in one and the same injection device.

The sequence of operation would thus be that the user first set the dose to be ejected by rotation of the rotatable dose setting element which moves the rotatable display element helically.

Once the rotatable display element reaches a predetermined position, whereby a predetermined minimum dose is set, the rotatable display element activates the locking mechanism to unlock the device.

In the unlocked state, the user then depresses the injection button which courses the release member to lock to the rotatable drive member thus holding the injection button in the depressed position.

Once the full dose has been ejected in one stroke and the torque of the torsion spring is sufficiently low e.g. zero, the return spring pulls back the injection button to the initial position which also causes the release element to be released from the rotatable drive member.

It has shown to be beneficial that the user cannot pause the ejection as it is known from conventional spring driven injection devices, because if that was possible the locking mechanism would be re-activated before the rotatable display element would reach its initial zero position. The user would thus be forced to set a new dose in order to activate the blocking structure and since this new dose would then be set from the paused position of the rotatable display element it would most likely result in an erroneous dose being set.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and preferably connected to a hub made from a suitable material e.g. a polymer. A needle cannula could however also be made from a polymeric material or a glass material.

As used herein, the term "Liquid drug" is meant to encompass any drug-containing flowable medicine capable of being passed through a delivery means such as a hollow needle cannula in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the primary container actually containing the liquid drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end of the cartridge is typically closed by a plunger or piston made from rubber or a suitable polymer. The plunger or piston can be slidable moved inside the cartridge. The space between the pierceable membrane and the movable plunger holds the liquid drug which is pressed out as the plunger decreased the volume of the space holding the liquid drug.

The cartridges used for both pre-filled injection devices and for durable injections devices are typically factory filled by the manufacturer with a predetermined volume of a liquid drug. A large number of the cartridges currently available contains either 1.5 ml or 3 ml of liquid drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. Usually the cartridge which has been filled by the manufacturer with a specific amount of liquid drug is secured in a cartridge holder which is then permanently connected in a housing structure such that the cartridge cannot be exchanged.

This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using prefilled injection devices an average user might require as many as 50 to 100 injection devices per year whereas when using durable injection devices one single injection device could last for several years, however, the average user would require 50 to 100 new cartridges per year.

A "Multi-Use Fixed Dose" injection device is meant to define an injection device which is able to deliver a pre-defined plurality (i.e. more than one) of doses which are substantially identical in volume. The liquid drug contained in the cartridge is thus expelled in a number of substantially identical dose volumes. In one example the cartridge could e.g. contain 3 ml of liquid drug which could e.g. be expelled in 6 identical dose volumes each of 0.5 ml. The number of equally sized doses are often 2 to 8, and preferably 4 to 6 identical dose volumes. A multi-use fixed dose injection device can either be pre-filled such that the injection device is discarded after the predefined number of dose volumes has been expelled or it can be a durable injection device enabling the user to change the cartridge and expel a new series of equally sized doses volumes from the new cartridge.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The actual spring for the spring drive is usually strained by the user during dose setting, however, such springs are usually pre-strained with a low force in order to avoid problems of delivering very small doses. Alternatively, the spring can be fully preloaded by the manufacturer with a preload sufficient to empty the entire drug cartridge though a number of doses. Typically, the user activates a latch mechanism provided either on the surface of the housing or at the proximal end of the injection device to release—fully or partially—the force accumulated in the spring when carrying out the injection.

The term "Permanently connected" or "permanently embedded" as used in this description is intended to mean that the parts, which in this application is embodied as a cartridge permanently embedded in the housing, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

Figure 1:
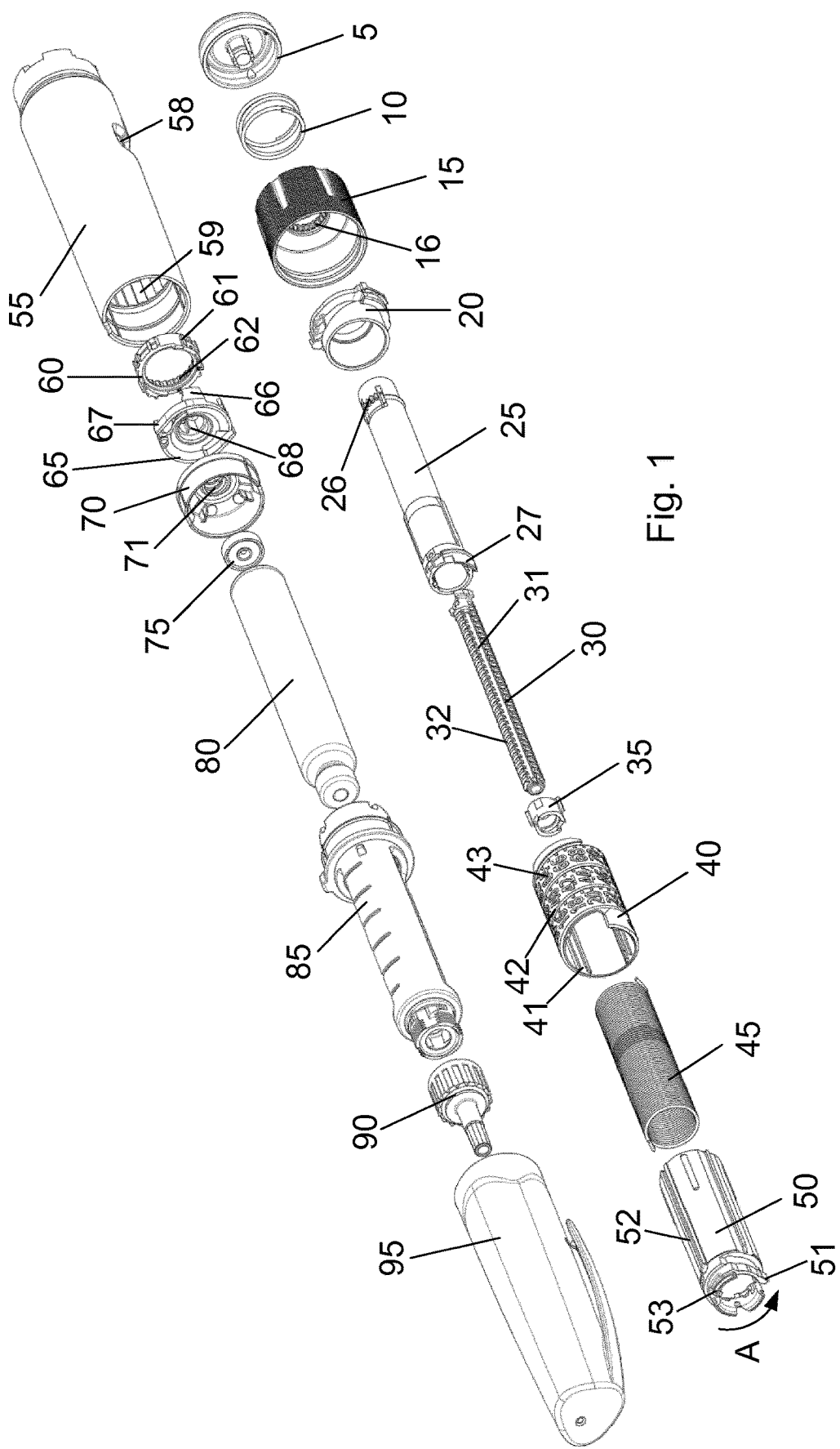
FIG. 1 show an exploded view of an example of a prior art torsion spring driven injection device.

The figures are schematic and simplified for clarity, and they just show details, which are essential to the understanding of the invention, while other details are left out.

Throughout, the same reference numerals are used for identical or corresponding parts.

DETAILED DESCRIPTION OF EMBODIMENT

When in the following terms as "upper" and "lower", "right" and "left", "horizontal" and "vertical", "clock-wise" and "counter clock-wise" or similar relative expressions are used, these only refer to the appended figures and not to an actual situation of use. The shown figures are schematic representations for which reason the configuration of the different structures as well as their relative dimensions are intended to serve illustrative purposes only.

In that context it may be convenient to define that the term "distal end" in the appended figures is meant to refer to the end of the injection device securing the needle cannula and pointing towards the user during injection, whereas the term "proximal end" is meant to refer to the opposite end usually carrying the injection button as depicted in FIG. 1. Distal and proximal is meant to be along an axial orientation extending along the longitudinal axis (X) of the injection device as also disclosed in FIG. 2.

Figure 2:
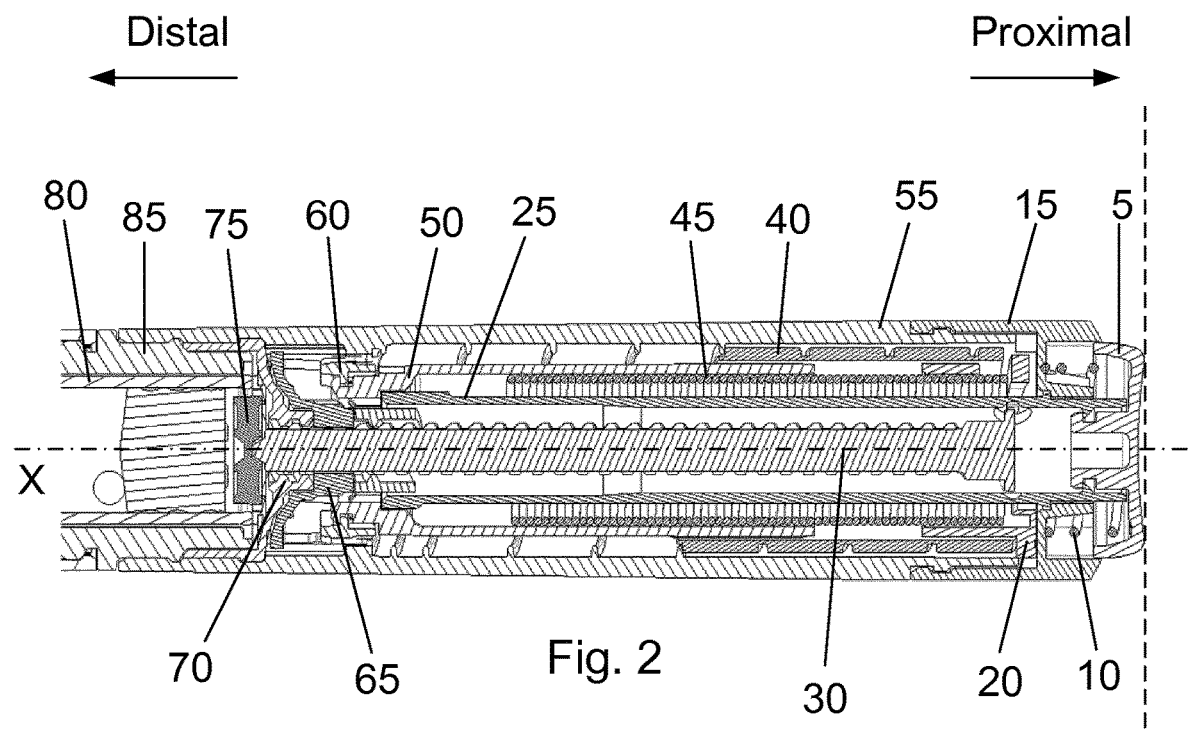
FIG. 2 show a cross-sectional view of the proximal part of the injection device of FIG. 1 during dose setting.
Figure 3:
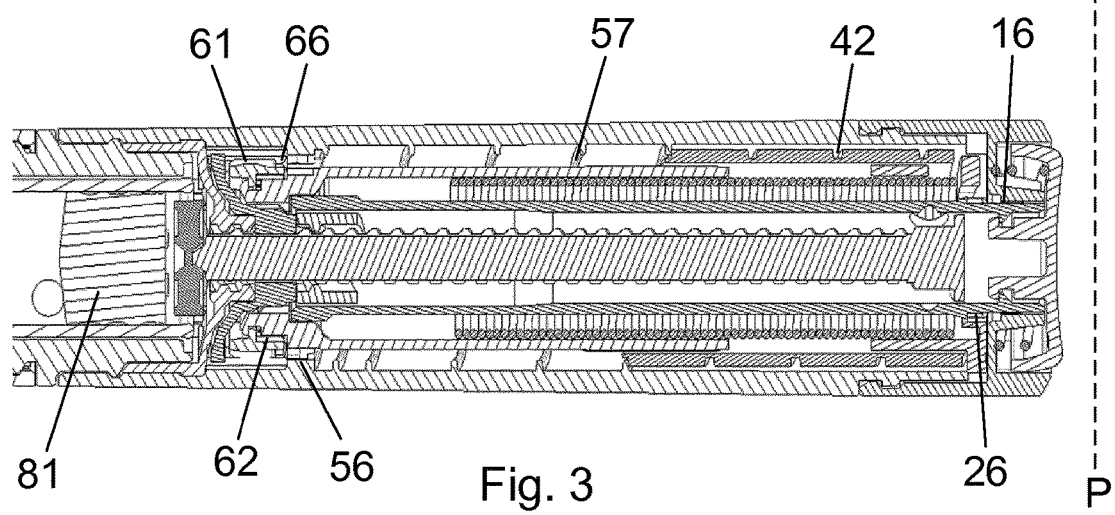
FIG. 3 show a cross-sectional view of the proximal part of the injection device of FIG. 1 during dose expelling.

FIGS. 1, 2 and 3 discloses the torsion spring driven injection device also disclosed in WO 2014/161952. This automatic injection device is being manufactured by Novo Nordisk NS and sold under the trade name FlexTouch®.

Seen from the proximal end in FIG. 1 this injection device comprises
a injection button 5,
a return spring 10,
a dose dial 15,
a spring base 20,
a reset tube 25,
a piston rod 30,
a EoC counter 35,
a scale drum 40,
a torque spring 45,
a ratchet tube 50,
a base part 55,
a clutch 60,
a piston rod driver 65,
a nut part 70,
a piston washer 75,
a cartridge 80,
a cartridge holder 85,
a pen needle 90,
a protective cap 95.

The dose setting- and injection mechanism is built in a housing structure which basically comprises the base part 55 and the cartridge holder part 85. The cartridge 80 containing the liquid drug is secured in the cartridge holder part 85 which is locked by the nut part 70. Proximally the base part 55 is closed by the spring base 20. Together these four parts; spring base 20, base part 55, nut part 70 and cartridge holder part 85 makes up the housing structure in the disclosed example. The housing structure could alternatively be made from other parts which could be connected in many different ways. It would also be possible to make the housing structure from a different number of parts or even to mould the housing structure as one unit.

The torsion spring 45 disclosed is a helical coiled metallic spring which is encompassed between the spring base 20, which is an inrotatable part of the housing structure, and the rotatable ratchet tube 50 at the distal end. When the ratchet tube 50 is rotated relatively to the housing structure a torque is thus built and stored in the torsion spring 45.

Dose Setting

Dose setting is disclosed in FIG. 2. Whenever the user wants to set the size of the dose of liquid drug to be ejected, the user rotates the dose dial 15. The dose dial 15 is rotationally coupled to the reset tube 25 by a toothed interface 16, 26 (see e.g. FIG. 1) such that the dose dial 15 and the reset tube 25 rotates together during dose setting.

The reset tube 25 is further rotationally coupled to the ratchet tube 50 which thus also rotates together with the dose dial 15 and the reset tube 25 during dose setting. The coupling between the ratchet tube 50 and the reset tube 25 is preferably such that the two parts 25, 50 is axially locked to each other but able to rotate a few degrees relatively to each other for lowering a set dose as will be explained. However, the two parts 25, 50 could alternatively be moulded as one unitary part in which case it would not be possible to regret and lower a set dose.

As seen in the FIGS. 1 to 3, the clutch 60 is on the outer surface provided with a number of outwardly pointing teeth 61 which during dose setting (FIG. 2) is engaged by similar teeth 56 provided inside the base part 55 of the housing structure such that the clutch 60 is kept inrotatable during dose setting.

Axially the clutch 60 is clicked on to the ratchet tube 50 such that the ratchet tube 50 and the clutch 60 moves together axially. However, this click fit is designed such that the clutch 60 is rotatable in relation the clutch 60.

Internally the clutch 60 is provided with a toothed ring 62 which is engaged by a flexible arm 51 provided distally on the ratchet tube 50 (any number of flexible arms 51 can be provided). This engagement allows the ratchet tube 50 to rotate in one direction only (in relation to the clutch 60 which is anchored in the housing structure during dose setting). In the attached drawings this allowed direction is the clock-wise direction (when the injection device is viewed from the proximal end) however this is only in the given example and could be the opposite direction if wanted. The allowed direction indicated by the arrow "A" in FIG. 1 is the direction that strains the torsion spring 45 which is encompassed between the spring base 20 and the ratchet tube 50. A torque is thus stored in the torsion spring 45 during rotation of the dose dial 15 and the engagement between the flexible arm 51 on the ratchet tube 50 and the toothed ring 62 inside the clutch 62 prevents this torque from being released.

The spring base 20 is inrotatable secured to the base part 55 of the housing structure such that the torsion spring 20 is strained when the ratchet tube 50 is rotated in the clock-wise direction.

The ratchet tube 50 is on the outer surface provided with ridges 52 which engage corresponding longitudinal recesses 41 provided on the inner surface of the scale drum 40. This interface forces the scale drum 40 to rotate together with the ratchet tube 50 at all times.

The scale drum 40 is further provided with a helical thread 42 on the outer surface which engages an internal thread 57 inside the base part 55 of the housing structure such that the scale drum 40 move helically when rotated. This helical movement of the scale drum 40 brings the indicia 43 printed in a helical pattern into the range of the window 58 in the base part 55 such that the user can visually follow the dose setting.

Should the user by accident set a dose size higher than what is actually required it is possible to lower the set dose by rotating the dose dial 15 in the opposite direction as explained below.

Dose Lowering

When the user regrets a set dose and wants to lower a set dose, the user rotates the dose dial 15 in the counter clock-wise direction (also when viewed form a proximal position) which rotation is transformed to a rotation of the reset tube 25 also in the counter clock-wise direction.

The reset tube 25 is coupled to the ratchet tube 50 such that these two elements 25, 50 are axially locked to each other but able to rotate a few degrees relatively to each other.

However, the ratchet tube 50 is engaged with the clutch 60 through the flexible arm 51 engaging the toothed ring 62 of the clutch 60, and the clutch 60 is rotationally secured in the housing structure by the interface between the teeth 61 and inwardly pointing teeth 56 in the base part 55 of the housing structure. The ratchet tube 50 is thus not immediately rotatable in the direction lowering the set dose.

Distally the reset tube 25 is provided with an axially extending key 27 which engages on the outside of the flexible arm 51 which flexible arm 15 is pressed toward the centre line X when the reset tube 25 is rotated counter clock-wise a few degrees relatively to the ratchet tube 50 to thereby lower the set does. This dial-down mechanism is described in more details in e.g. U.S. Pat. No. 9,132,239.

The impact by the key 27 on the flexible arm 51 thus forces the flexible arm 51 out of engagement with the clutch 60 such that the torque of the torsion spring 80 is able to rotate the ratchet tube 50 in the counter clock-wise direction. Since the rotational speed of the ratchet tube 50 when impacted by the torque of the torsion spring 45 is higher than the rotational speed of the reset tube 25 operated by the user, the flexible arm 51 re-engages the first previous teeth in the toothed ring 62. It is thus possible to lower the set dose size incrementally by rotating the dose dial 15 in a direction opposite to the direction used when setting a dose (the counter clock-wise direction in the example).

Both during dose setting and when regretting the set dose, the scale drum 40 rotates helically forced by the ratchet tube 50 such that the user at any time can inspect the resulting set dose in the window 58.

Once the correct dose has been reached, the user inserts the pen needle 90 through the skin and injects the set dose.

Injecting

The injection is performed by pushing the injection button 5 a distance in the distal direction against the bias of the return spring 10 which distance is indicated by the dashed line "P" in FIG. 2 and FIG. 3.

The injection button 5 is click-fitted to the reset tube 20 as disclosed in FIG. 3 which show the situation during injection. The injection button 5 thus also moves the reset tube 20 in the distal direction.

As further seen in FIG. 3, the ratchet tube 50 is axially coupled to the reset tube 20 and the clutch 60 is coupled to the ratchet tube 50. The result being that both the ratchet tube 50 and the clutch 60 is moved in the distal direction when the injection button 5 and the reset tube 20 are pushed distally by the user.

The distal movement of the clutch 60 disengages the outwardly pointing teeth 61 on the clutch 60 from the teeth 56 inside the base part 55 of the housing structure. Consequently, there is nothing holding the torque stored in the torsion spring 45 when the injection button 5 is pushed distally. The torque of the torsion spring 45 consequently rotates the ratchet tube 50 and the flexible arm 51 provided on the ratchet tube 50 transfers this rotation to a rotation of the clutch 60. The reset tube 20 also rotates together with the ratchet tube 50. This rotation occurs in the disclosed example in the anti clock-wise direction.

As seen in FIG. 1 the reset tube 20 engages the dose dial 15 with a toothed engagement 16, 26 such that when the reset tube 20 is moved distally this engagement disengages such that the dose dial 15 do not follow the rotation of the reset tube 20 during injection.

However, the scale drum 40 is constantly engaged with the ratchet tube 50 such that the scale drum 40 rotates helically back to its initial position when the ratchet tube 50 rotates during injection. Both FIG. 2 and FIG. 3 depicts the scale drum 40 in the "zero" position.

When the ratchet tube 50 together with the clutch 60 are moved distally out of engagement with the base part 55 of the housing structure, the teeth 61 provided on the clutch 60 are moved axially into engagement with corresponding teeth 66 provided on the piston rod driver 65.

The torque of torsion spring 45 is thus transferred to a rotation of the piston rod driver 65 which is further provided with one or more one-way arms 67 engaging a toothed periphery 59 inside the base part 55 of the housing structure only allowing rotation of the piston rod driver 65 in one rotational direction (anti clock-wise in the disclosed example when viewed form a proximal position).

Internally the piston rod driver 65 is provided with one or more inwardly pointing ridges 68 engaging longitudinal grooves 31 in the piston rod 30 such that the piston rod 30 is forced to rotate with the piston rod driver 65 during injection.

The rotation of the ratchet tube 50, the scale drum 40, the clutch 60 and the reset tube 25 under the force of the torque of the torsion spring 45 and the resulting rotation of the piston rod 30 screws the piston rod 30 helically in the distal direction due to the engagement between the thread 71 of the nut part 70 and the thread 32 of the piston rod 30.

Distally the piston rod 30 pushes on a piston rod foot 75 which transfers the forward movement of the piston rod 30 to a forward movement of the plunger 81 inside the cartridge 80 which again forces a volume of the liquid drug out through the lumen of the pen needle 90.

As best seen in FIG. 1 the scale drum 40 carries a number of indicia 43 printed in a helical row on the outer surface. These indicia 43 pass by the window 58 in the housing structure both during dose setting, during dose lowering and during injection. Any random number of indicia 43 can be provided and in the example disclosed in FIG. 1 these indicia 43 are Arabian number in the range from 0 to 70. Typically, these numbers indicate some kind of units related to the liquid drug contained in the cartridge 80, but obviously any and all kind of indicia can be used.

The scale drum 40 is fixed to the ratchet tube 50 in the longitudinal direction and threaded to the base part 55 of the housing structure such that the scale drum 40 move helically when the ratchet tube 50 is rotated as explained. When the dose intended to be ejected has been reached the user pushes the injection button 5 in the distal direction to thereby eject the set dose. The injection button 5 together with the reset tube 25 and the ratchet tube 50 are movable in the distal direction for any given dose size in the example disclosed in FIGS. 1 to 3.

Further, an End-of-Content and safety nut 35 is provided, the use of which is explained in EP 1,909,870 and in EP 1,909,871.

Minimum Dose

In the following example of the invention which is disclosed in the FIGS. 4 to 7 the same numerals has been used for the same or corresponding physical elements.

For some liquid drugs it is beneficial if the dose to be ejected can only be released when a certain and predetermined minimum dose size has been set by the user.

Figure 4:
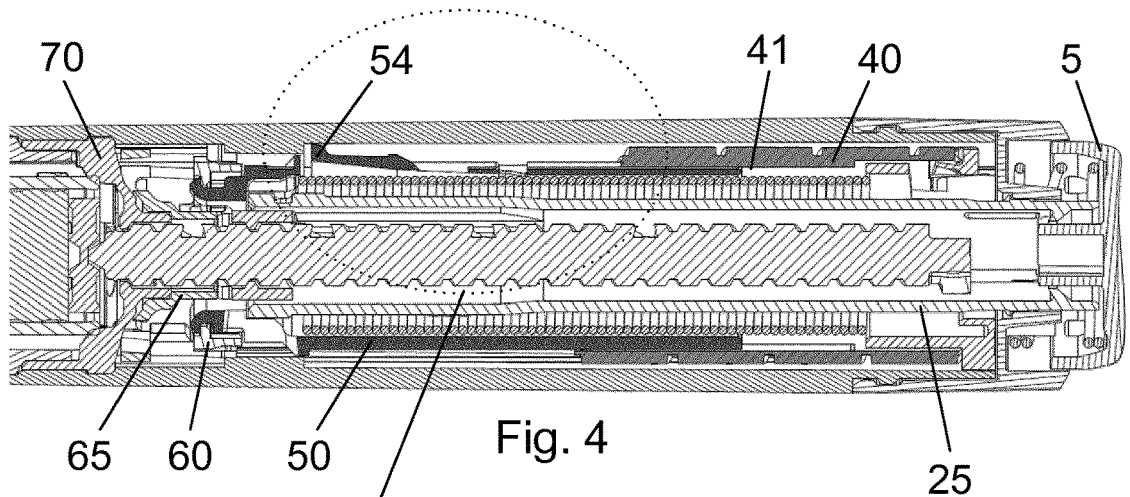
FIG. 4 show a cross-sectional view of the proximal part of a torsion spring driven injection device with the blocking structure of the present invention.
Figure 5:
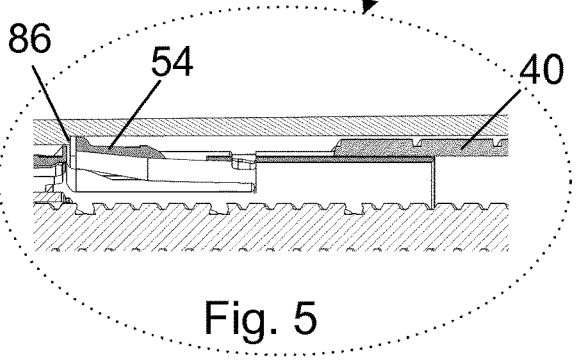
FIG. 5 show the details of the blocking structure encircled in FIG. 4.
Figure 6:
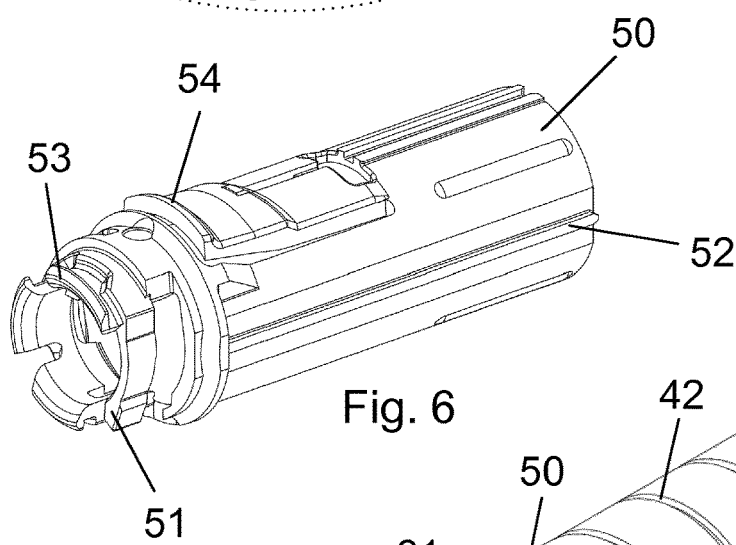
FIG. 6 show a perspective view of the ratchet tube with a blocking arm.

In order to make sure that such minimum dose size has been set the ratchet tube 50 is provided with a locking arm 54 as disclosed e.g. in FIG. 6. This locking arm 54 abut a flange 86 provided on an inner surface of the housing structure as disclosed in FIG. 4 and in FIG. 5 wherein FIG. 4 is a cross-sectional view of the injection device with the scale drum 40 in the initial "zero" position and FIG. 5 show details of the engagement between the locking arm 54 and the flange 86.

The flange 86 can be provided on any part of the housing structure but is in the disclosed example provided on an inner surface of the base part 55.

As previously explained, the scale drum 40 is threaded to the base part 55 of the housing by threads 42 on the outer surface of the scale drum 40 engaging similar threads 57 inside the base part 55 of the housing structure. Due to this engagement the scale drum 50 is able to move helically in relation to the housing structure when rotated.

The rotation of the scale drum 40 is introduced by rotation of the ratchet tube 50 which externally is provided with ridges 52 engaging longitudinal recesses 41 on the inner surface of the scale drum 40.

Figure 7:
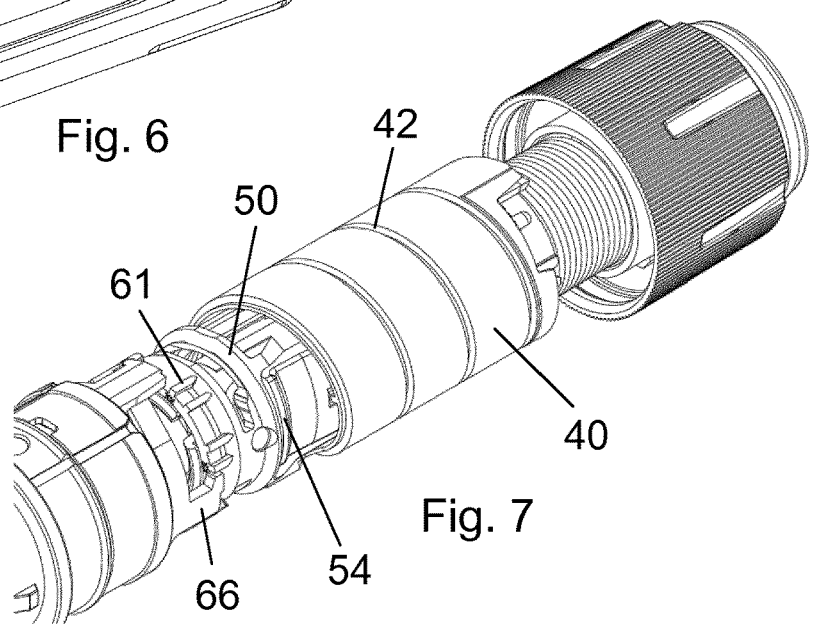
FIG. 7 show a perspective view of the interior of the injection device according to the invention with the proximal part of the housing structure visually removed.

During helical movement of the scale drum 40 along the ratchet tube 50, the scale drum 40 will at a specific position engage with the locking arm 54 as best seen in FIG. 7 which will thus be bended away from the flange 86 inside the housing structure. When this happens, the ratchet tube 50 is able to move in the distal direction as required in order to release a dose.

FIG. 7 disclose the situation in which the minimum dose has been set. The scale drum 40 has moved helically in the distal direction to a position wherein the scale drum 40 now activates the flexible arm 54 which is thus bended inwardly and away from the flange 86 which allows the ratchet tube 50 carrying the clutch to be moved axially in the distal direction relatively to the housing structure.

In the depicted embodiment the scale drum 40 moves helically in the distal direction during dose setting and moves proximally during dose expelling. The situation disclosed in FIG. 7 is thus when a dose has been set and the set dose has a sufficient size such that the scale drum 40 has actually bended the flexible arm 54 inwardly. It is noted that the shape of the flexible arm 54 can be designed to accommodate the engagement with the scale drum 40.

As explained, the ratchet tube 50 together with the clutch 60 is moved in the distal direction when the user pushes the injection button 5 thus moving the reset tube 25 distally.

Henceforth, a dose can only be released when the scale drum 40 has reached a specific point which is determined by the relative position of the locking arm 54 and the flange 86.

On the specific physical position on the scale drum 40 viewable in the window 58 where the locking arm 54 is bended away from the flange 86 inside the housing structure a specific indicia indicating the unlocked position can be provided.

Release Mechanism

Figure 8:
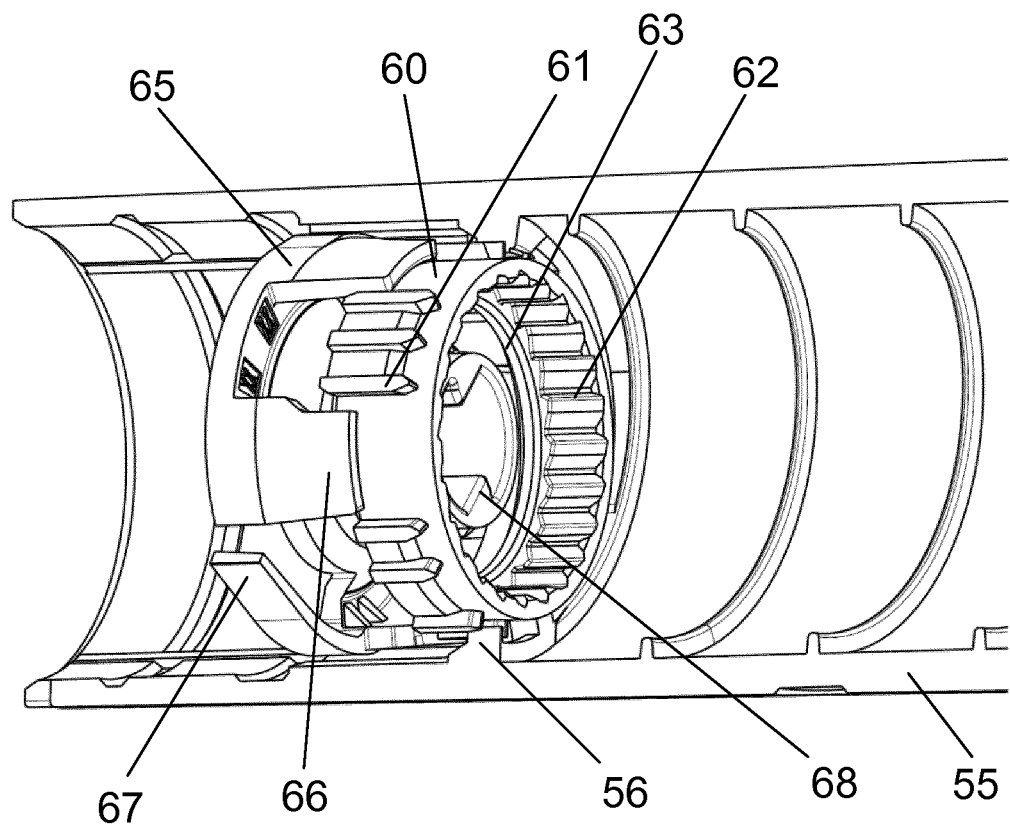
FIG. 8 show a perspective cut open view of the prior art engagement between the release element (clutch) and the piston rod driver during dose setting.
Figure 9:
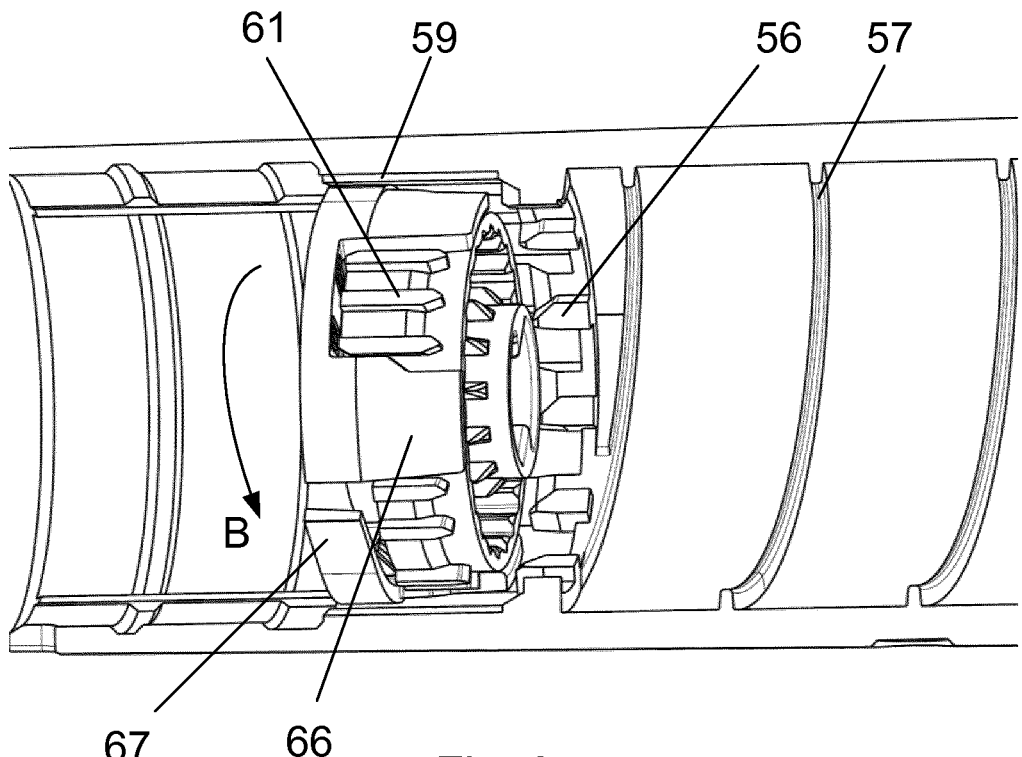
FIG. 9 show a perspective cut open view of the prior art engagement between the release element (clutch) and the piston rod driver during dose expelling.

The release mechanism is disclosed in details in FIG. 8 and in FIG. 9. FIG. 8 show the position of the clutch 60 during dose setting. In this position the outwardly pointing teeth 61 are locked in the housing structure such that the clutch 60 is kept inrotatable. As seen in FIG. 8, a number of inwardly pointing teeth 56 provided on the inside surface of the housing structure engages the teeth 61 on the clutch 60 to prevent rotation of the clutch 60 during dose setting.

The clutch 60 is, as previously mentioned, axially coupled to the ratchet tube 50 by having an annular recess 63 being engaged by a radial flange 53 provided distally on the ratchet tube 50. The clutch 60 is thus able to rotate relatively to the ratchet tube 50 but is forced to move axially together with the ratchet tube 50 during dosing.

In the dose setting position disclosed in FIG. 8, the user rotates the dose dial 15 and thereby the reset tube 25 to set the size of the dose to be ejected, this rotation is transferred to a rotation of the ratchet tube 50 which courses the flexible arm 51 on the ratchet tube 50 to click over the internal teeth in the toothed ring 62 thus providing the user with an audible signal that a dose is being set.

Once the correct dose has been set, the user pushes the injection button 5 against the bias of the return spring 10 which moves the reset tube 25, the ratchet tube 50 and the clutch 60 in the distal direction into the released position disclosed in FIG. 9.

In this released position, the clutch 60 is released from the housing structure (i.e. the teeth 61 dis-engages from the teeth 56) and engages the corresponding teeth 66 of the piston rod driver 65. The torque stored in the torsion spring 45 is thereby applied onto a rotation of the ratchet tube 50 which via the flexible arm 51 transfers the torque to a rotation of the clutch 60.

The engagement between the teeth 61 of the clutch 60 and the corresponding teeth 66 on the piston rod driver 65 thus makes the piston rod driver 65 rotate as indicated by the arrow B in FIG. 9. This rotation occurs in the counter clock-wise direction (in the given example) and the one-way arms 67 clicks over the toothed periphery 59 of the base part 55 of the housing structure. This provides a distinct sound to the user that a dose is being distributed.

The torque is thus transferred through the abutment between the teeth 61 on the release element 60 and the corresponding teeth 66 on the piston rod driver 65.

Should the user want to pause the injection before the set does has been ejected, this is simply done by removing the force applied to the injection button 5 e.g. by removing the finger from the injection button 5. This will course the return spring 10 to move the injection button 5 back in the proximal direction which will also move the reset tube 25 proximally. Since the reset tube 25 is axially coupled to the ratchet tube 50, the ratchet tube 50 will also be moved proximally which thus moves the clutch 60 back into the position disclosed in FIG. 8 wherein the teeth 61 are moved into engagement with the teeth 56 in the base part 55 of the housing structure thus halting the dosing.

However, sometimes it has proven to be beneficial if the user cannot pause the dosing such that once the injection button 5 has been activated the complete set dose is ejected in one stroke.

Full Dose Release

If the user removes the finger from the injection button 5 in the example disclosed in FIG. 4, the expelling of the dose will immediately stop as the clutch 60 moves proximally and locks to the housing structure, however since the locking mechanism 54, 86 has been activated when the scale drum 40 has moved proximally it is no longer possible to release the remaining part of the set dose. In such example it is thus beneficial if the user cannot stop the ejection before the full dose has been fully expelled.

Figure 10:
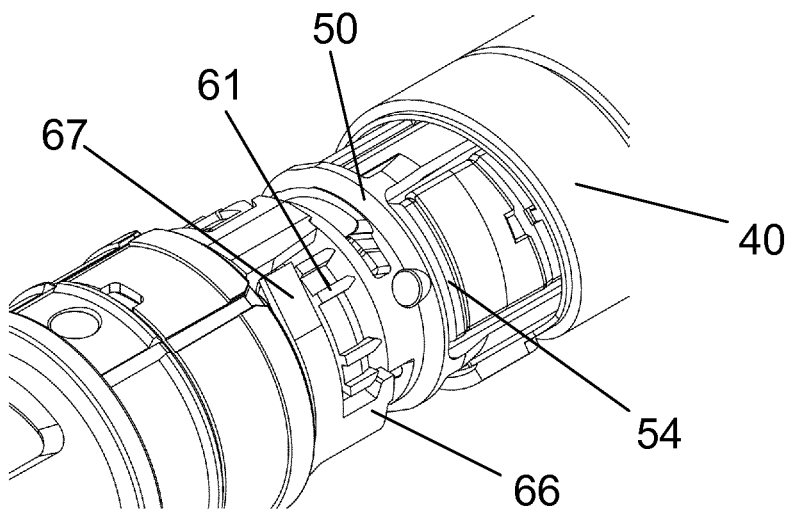
FIG. 10 show a perspective cut open view of the engagement between the release element (clutch) and the piston rod driver during dose expelling in an example of the invention.
Figure 11:
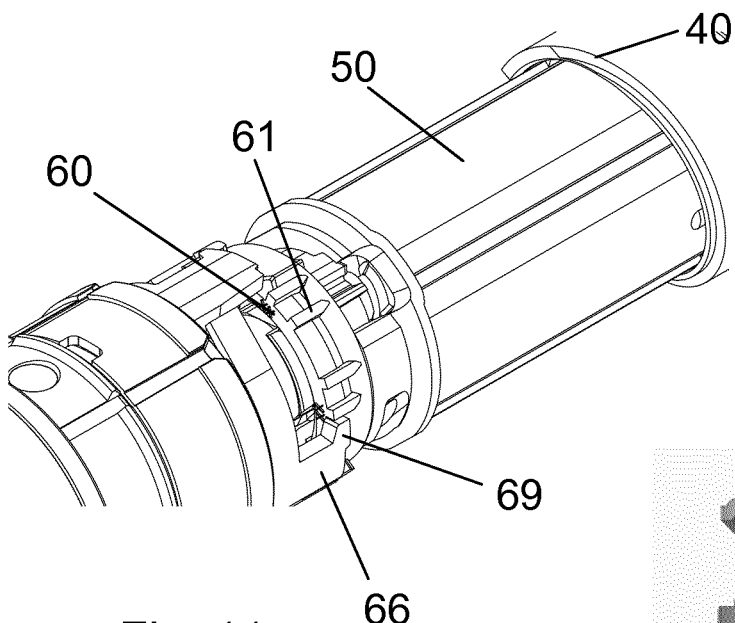
FIG. 11 show a perspective cut open view of the engagement between the release element (clutch) and the piston rod driver following dose expelling i.e. in the non-dosing position, in an example of the invention.

An example making this possible is disclosed in FIG. 10 and in FIG. 11. In this example, the corresponding teeth 66 is proximally provided with a radial extension 69 such that when the corresponding teeth 66 is moved into the dosing position disclosed in FIG. 10 this radial extension 69 grips proximally on the teeth 61.

In FIG. 10, the scale drum 40 is in the set position as it has been moved in the distal direction and since the scale drum 40 has released the locking arm 54 it is thus possible to move the release element 60 distally into engagement with the rotatable drive element 65.

As the radial extension 69 grip behind the teeth 61 as shown in FIG. 10, the teeth 61 cannot move in the proximal direction as long as the sidewall of the teeth 61 is urged against the corresponding teeth 66 with a sufficient force. The rotational force urging the teeth 61 against the corresponding teeth 66 arises from the torque of the torsion spring 45 rotationally driving the clutch 60. It is thus not possible for the return spring 10 to pull the clutch 60 with the teeth 61 out of the engagement with the corresponding teeth 66 and the radial extension 69 as long as the torque applied by the torsion spring 45 is over a certain threshold value.

However, once the torque applied by the teeth 61 onto the corresponding teeth 66 falls below the defined threshold value which it does when the clutch 60 stop to rotate, the teeth 61 is able to slide proximal pass the radial extension 69.

Should the user therefore remove the finger from the injection button 5 during injection, the injection button 5 will remain depressed and the clutch 60 will keep rotating as long as the torque stored in the torsion spring 45 rotates the ratchet tube 25 and the clutch 60. This rotation will continue until the torque falls below the threshold value. This happens either when the stored torque has been used or when the scale drum 40 strikes on an end stop such that the scale drum 40 and the ratchet tube 50 cannot rotate any more. Thus once the torque stored in the torsion spring 45 drops below the defined threshold value, the clutch 60 will stop to rotate and as no significant torque is now applied onto the abutment between the teeth 61 and the corresponding teeth 66, the teeth 61 is able to slide pass by the radial extension 69 and slide back in the proximal direction to the locked position of FIG. 11. In this position, the scale drum has returned to the initial position.

Figure 12:
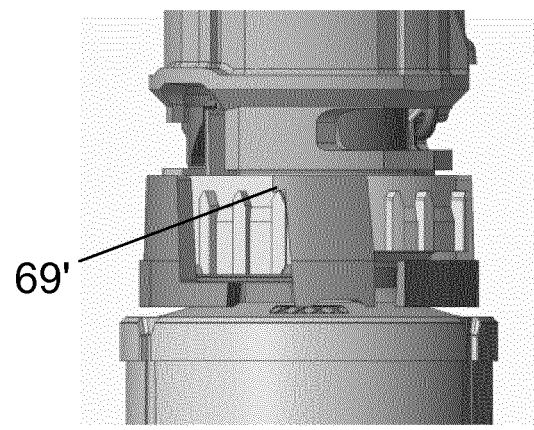
FIG. 12 show a side view of the engagement between the release element (clutch) and the rotatable drive element in yet another example of the invention.

In a further example disclosed in FIG. 12, the radial extension 69' has a further axial prolongation sloping in the distal direction such that the teeth 61 cannot be released from the corresponding teeth 66 at any time. This means that once an engagement between the two teeth 61, 66 has been established this engagement cannot be undone. The injection device is henceforth a single dose injection device since the release element 60 cannot be released from the housing structure more than once.

Some preferred embodiments have been shown in the foregoing, but it should be stressed that the invention is not limited to these, but may be embodied in other ways within the subject matter defined in the following claims.

The invention claimed is:

1. A torsion spring driven injection device for ejecting at least one dose of a liquid drug comprising:
   a housing structure securing a container containing the liquid drug to be ejected,
   a rotational dose setting element operable by a user for setting the size of a set dose to be ejected,
   a rotatable dose setting structure transferring rotation from the dose setting element to a straining of a torsion spring such that a torque is stored in the torsion spring upon rotation of the dose setting element,
   a rotatable display element arranged to follow rotation of the dose setting structure and helically movable relatively to the housing structure from an initial position to a dosing position, wherein the set dose is indicated by indicia carried by the rotatable display element,
   a piston rod arranged in a longitudinal direction (X) and movable in a distal direction to expel the set dose from the container,
   a rotatable drive element engaging the piston rod and adapted to move the piston rod in the distal direction upon rotation of the rotatable drive element,
   an axially movable release element for releasing the torque stored in the torsion spring to rotate the rotatable drive element,
   wherein,
   the injection device further comprises a blocking structure which is operable between a first position and a second position, and wherein
   the blocking structure in the first position prevents axial movement of the release element and in the second position allows axial movement of the release element,
   and which blocking structure is operational by the rotatable display element,
   such that whenever the rotatable display element is rotated to a specific axial position and/or rotational position it activates the blocking structure such that the release element becomes axially movable to thereby release the set dose.

2. The torsion spring driven injection device according to claim 1, wherein the rotatable display element is coupled to the dose setting structure such that the rotatable display element follows rotation of the dose setting structure.

3. The torsion spring driven injection device according to claim 2, wherein the dose setting structure comprises a ratchet tube having the rotatable display element coupled thereto.

4. The torsion spring driven injection device according to claim 1, wherein the rotatable display element is guided relatively to the housing structure by a helical interface such that the rotatable display element moves helically when rotated.

5. The torsion spring driven injection device according to claim 1, wherein a ratchet tube and the release element are coupled to each other such that the release element follows axial movement of the ratchet tube.

6. The torsion spring driven injection device according to claim 1, wherein a ratchet tube is coupled to follow axial movement of a reset tube comprised in the dose setting structure.

7. The torsion spring driven injection device according to claim 1, wherein the release element is axially movable in the distal direction into engagement with the rotatable drive element by axial movement of the dose setting structure during dosing.

8. The torsion spring driven injection device according to claim 1, wherein the dose setting structure is provided with one or more locking arms engaging the housing structure to thereby prevent axial movement of the dose setting structure.

9. The torsion spring driven injection device according to claim 8, wherein the rotatable display element activates the locking arm to move out of engagement with the housing structure at a specific position of the rotatable display element relatively to the housing structure.

10. The torsion spring driven injection device according to claim 9, wherein the housing structure on the inner surface is provided with a flange structure engaging the locking arm to prevent axial movement of the ratchet tube and wherein, the rotatable display element moves the locking arm away from the flange structure at a specific position of the rotatable display element relatively to the housing structure.

11. The torsion spring driven injection device according to claim 1, wherein coupling between the ratchet tube and the rotatable display element is by groove and tongue engagement.

12. A torsion spring driven injection device for ejecting at least one dose of a liquid drug comprising:
- a housing structure securing a container containing the liquid drug to be ejected,
- a rotational dose setting element operable by a user for setting the size of the dose to be ejected,
- a rotatable dose setting structure transferring rotation from the dose setting element to a straining of a torsion spring such that a torque is stored in the torsion spring upon rotation of the dose setting element,
- a rotatable display element arranged to follow rotation of the dose setting structure and helically movable relatively to the housing structure from an initial position to a dosing position, wherein the set dose is indicated by the rotatable dose setting element,
- a piston rod arranged in a longitudinal direction and movable in a distal direction to expel the set dose out from the container,
- a rotatable drive element engaging the piston rod and adapted to move the piston rod in the distal direction upon rotation of the rotatable drive element,
- an axially movable release element for releasing the torque stored in the torsion spring to rotate the rotatable drive element,
- wherein the release element is provided with one or more teeth axially engaging corresponding teeth provided on the rotatable drive element and a torque arising from the torsion spring during dosing is transferred from the one or more teeth of the release element to the corresponding teeth on the rotatable drive element such that a rotation of the release element during dosing is transferred to a rotation of the rotatable drive element,
- and wherein the one or more teeth on the release element are slidable in the axial direction in relation to the corresponding teeth on the rotatable drive element, wherein,
at least one of the corresponding teeth on the rotatable drive element proximally is provided with a radial extension which hinders the teeth and the release element from sliding in the axial direction in relation to the corresponding teeth on the rotatable drive element when a torque above a certain threshold value is being applied to the corresponding teeth.

13. The torsion spring driven injection device according to claim 12, wherein the transformation between the corresponding teeth and the radial extension comprises a sloped surface along which the one or more teeth can slide when no torque is applied to the corresponding teeth.

14. The torsion spring driven injection device according to claim 12, wherein the radial extension is shaped such that it permanently locks the teeth and the release element from axial movement.

15. The torsion spring drive injection device according to claim 12, wherein between the teeth and the radial extension comprises a sloped surface along which the one or more teeth can slide when no torque is applied to the corresponding teeth.

16. The torsion spring drive injection device according to claim 12, wherein the radial extension is shaped such that it locks the teeth and the release element from axial movement.

17. The torsion spring driven injection device according to claim 12, wherein the release element is on an outer surface.

* * * * *

UNITED STATES PATENT AND TRADEMARK OFFICE
CERTIFICATE OF CORRECTION

| | | |
|---|---|---|
| PATENT NO. | : 12,109,398 B2 | Page 1 of 1 |
| APPLICATION NO. | : 17/286845 | |
| DATED | : October 8, 2024 | |
| INVENTOR(S) | : Claus Urup Gjoedesen et al. | |

It is certified that error appears in the above-identified patent and that said Letters Patent is hereby corrected as shown below:

In the Claims

At Column 18, Claim number 15, Line number 24, please delete "drive" and insert --driven--.

At Column 18, Claim number 16, Line number 29, please delete "drive" and insert --driven--.

Signed and Sealed this
Twelfth Day of August, 2025

Coke Morgan Stewart
*Acting Director of the United States Patent and Trademark Office*